US011890146B2

(12) United States Patent
Zapata et al.

(10) Patent No.: US 11,890,146 B2
(45) Date of Patent: Feb. 6, 2024

(54) ILLUMINATION SYSTEM AND METHOD FOR OBJECT TRACKING

(71) Applicant: Gentex Corporation, Zeeland, MI (US)

(72) Inventors: Jorge Zapata, Chagrin Falls, OH (US); Carlos Eduardo Vargas Silva, Antioquia (CO)

(73) Assignee: GENTEX CORPORATION, Zeeland, MI (US)

( * ) Notice: Subject to any disclaimer, the term of this patent is extended or adjusted under 35 U.S.C. 154(b) by 240 days.

(21) Appl. No.: 16/906,417

(22) Filed: Jun. 19, 2020

(65) Prior Publication Data

US 2020/0397528 A1 Dec. 24, 2020

Related U.S. Application Data

(60) Provisional application No. 62/863,905, filed on Jun. 20, 2019.

(51) Int. Cl.
| | |
|---|---|
| *G06T 7/20* | (2017.01) |
| *G06T 7/70* | (2017.01) |
| *G06T 7/00* | (2017.01) |
| *G06F 21/32* | (2013.01) |
| *A61B 90/30* | (2016.01) |
| *A61B 90/00* | (2016.01) |

(52) U.S. Cl.
CPC .......... *A61B 90/30* (2016.02); *A61B 90/361* (2016.02); *G06F 21/32* (2013.01); *G06T 7/0012* (2013.01); *G06T 7/20* (2013.01); *G06T 7/70* (2017.01); *G06T 2207/30196* (2013.01)

(58) Field of Classification Search
None
See application file for complete search history.

(56) References Cited

U.S. PATENT DOCUMENTS

| | | | |
|---|---|---|---|
| 4,639,838 A | 1/1987 | Kato et al. | |
| 5,347,431 A | 9/1994 | Blackwell et al. | |
| (Continued) | | | |

FOREIGN PATENT DOCUMENTS

| | | |
|---|---|---|
| CN | 107799171 A | 3/2018 |
| DE | 102017006529 A1 | 1/2019 |
| (Continued) | | |

OTHER PUBLICATIONS

Hunt, Barry "Introduction to UV Surface Disinfection" InfectionControl. tips, Jan. 21, 2016, https//infectioncontrol.tips/2016/01/21/1423/.

*Primary Examiner* — Tize Ma
(74) *Attorney, Agent, or Firm* — Price Heneveld LLP; Brian James Brewer

(57) ABSTRACT

An illumination system for monitoring and illuminating an operating region includes at least one light assembly including at least one illumination source configured to selectively direct a light emission in a portion of the operating region. At least one imager is configured to capture image data in a field of view in the operating region. A controller is in communication with the light assembly and the imager. The controller is configured to process image data captured in the field of view and identify a plurality of objects detected in the image data based on an object library. Track a location of each of the plurality of objects and store the location of each of the objects.

16 Claims, 5 Drawing Sheets

(56) References Cited

U.S. PATENT DOCUMENTS

| | | | |
|---|---|---|---|
| 6,079,862 A | 6/2000 | Kawashima et al. | |
| 6,471,363 B2 | 10/2002 | Howell et al. | |
| 6,496,595 B1 | 12/2002 | Puchek et al. | |
| 7,224,472 B2 | 5/2007 | Bauch et al. | |
| 7,706,683 B2 | 4/2010 | Rossner et al. | |
| 8,736,548 B2 | 5/2014 | Pryor | |
| 8,817,085 B2 | 8/2014 | Hiltl et al. | |
| 8,905,585 B2 | 12/2014 | Dallam et al. | |
| 9,222,257 B2 | 12/2015 | Dallam et al. | |
| 9,513,113 B2 | 12/2016 | Yang et al. | |
| 10,119,808 B2 | 11/2018 | Venkataraman et al. | |
| 10,194,990 B2 * | 2/2019 | Amanatullah | A61B 34/20 |
| 10,231,607 B2 | 3/2019 | Charles et al. | |
| 10,240,751 B2 | 3/2019 | Zapata et al. | |
| 10,277,842 B1 | 4/2019 | Cooper et al. | |
| 10,517,158 B2 | 12/2019 | Hallack et al. | |
| 10,757,369 B1 * | 8/2020 | Mukhopadhyay | H04N 7/181 |
| 2008/0117569 A1 | 5/2008 | Lee | |
| 2010/0172545 A1 * | 7/2010 | Lim | G01S 17/86 |
| | | | 382/106 |
| 2011/0019884 A1 * | 1/2011 | Blau | A61B 90/37 |
| | | | 382/128 |
| 2011/0026781 A1 * | 2/2011 | Osadchy | H04L 9/008 |
| | | | 382/118 |
| 2012/0206050 A1 | 8/2012 | Spero | |
| 2013/0113929 A1 | 5/2013 | DeLand | |
| 2016/0106354 A1 * | 4/2016 | Shudo | A61B 3/0091 |
| | | | 351/210 |
| 2017/0180720 A1 | 6/2017 | Jarc | |
| 2017/0367785 A1 | 12/2017 | Munari | |
| 2018/0341835 A1 * | 11/2018 | Siminoff | G06V 10/751 |
| 2019/0038362 A1 | 2/2019 | Nash et al. | |
| 2019/0060026 A1 | 2/2019 | Geerlings et al. | |
| 2019/0117809 A1 | 4/2019 | Katz | |
| 2019/0182415 A1 * | 6/2019 | Sivan | G06F 3/012 |

FOREIGN PATENT DOCUMENTS

| | | |
|---|---|---|
| JP | 2002324403 A | 11/2002 |
| JP | 2012196239 A | 10/2012 |
| KR | 20160007700 A | 1/2016 |
| KR | 20180057447 A | 5/2018 |
| WO | 0035402 | 6/2000 |
| WO | 2004100815 A2 | 11/2004 |
| WO | 2013111134 A1 | 8/2013 |

* cited by examiner

ILLUMINATION SYSTEM AND METHOD FOR OBJECT TRACKING

CROSS-REFERENCE TO RELATED APPLICATION

This application claims priority to and the benefit under 35 U.S.C. § 119(e) of U.S. Provisional Patent Application No. 62/863,905, filed on Jun. 20, 2019, entitled "SYSTEM AND METHOD FOR VISUALIZATION," the disclosure of which is hereby incorporated herein by reference in its entirety.

TECHNOLOGICAL FIELD

The present disclosure relates generally to an illumination and imaging system and, more particularly, relates to a vision-based illumination, object detection, and tracking system.

BACKGROUND OF THE INVENTION

Surgical settings can be complex due to the variety of operations and patients that may be served in a limited time. Such complexity may lead to errors in identification and patient processing. Accordingly, efficient methods to accurately identify patients and access patient records may be advantageous. The disclosure provides for an improved system to assist in limiting the complexity of medical suites and related activities.

SUMMARY OF THE INVENTION

In one aspect of the invention, an illumination system for a monitoring and illuminating an operating region is disclosed. The system comprises at least one light assembly comprising at least one illumination source configured to selectively direct a light emission in a portion of the operating region. At least one imager is configured to capture image data in a field of view in the operating region. A controller is in communication with the light assembly and the imager. The controller is configured to process image data captured in the field of view and identify a plurality of objects detected in the image data based on an object library, track a location of each of the plurality of objects, and store the location of each of the objects.

In another aspect of the invention, an illumination system for a monitoring and illuminating an operating region is disclosed. The system comprises at least one light assembly comprising an illumination source configured to selectively direct light emissions in a portion of the operating region and at one least imager configured to capture image data in a field of view in the operating region. A controller is in communication with the light assembly and the imager. The controller is configured to process image data captured in the field of view and identify a plurality of objects detected in the image data based on an object library and access object information for the plurality of objects. The controller is further configured to complete a balance determination of each of the plurality of objects over a period of time. The balance determination identifies a disposal, storage, or implant location of each of the objects.

In yet another aspect of the invention, an Illumination apparatus configured to illuminate an operating region is disclosed. The apparatus comprises at least one light assembly comprising at least one illumination source configured to selectively direct light emissions in a portion of the operating region and at least one imager configured to capture image data in a field of view in the operating region. A controller is in communication with the light assembly and the imager. The controller is configured to process image data captured in the field of view. The controller is further configured to identify a plurality of objects detected in the image data based on an object library and access object information for the plurality of objects. The object data identifies the plurality of objects as associated objects pre-approved for use in the operating region. The controller is further configured to compare the identified objects to the associated objects identified in the object information and, based on the comparison, identify unexpected objects in the library that are not preapproved.

These and other features, advantages, and objects of the present device will be further understood and appreciated by those skilled in the art upon studying the following specification, claims, and appended drawings.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity and conciseness.

In the drawings.

DETAILED DESCRIPTION OF EMBODIMENTS

Figure 1:
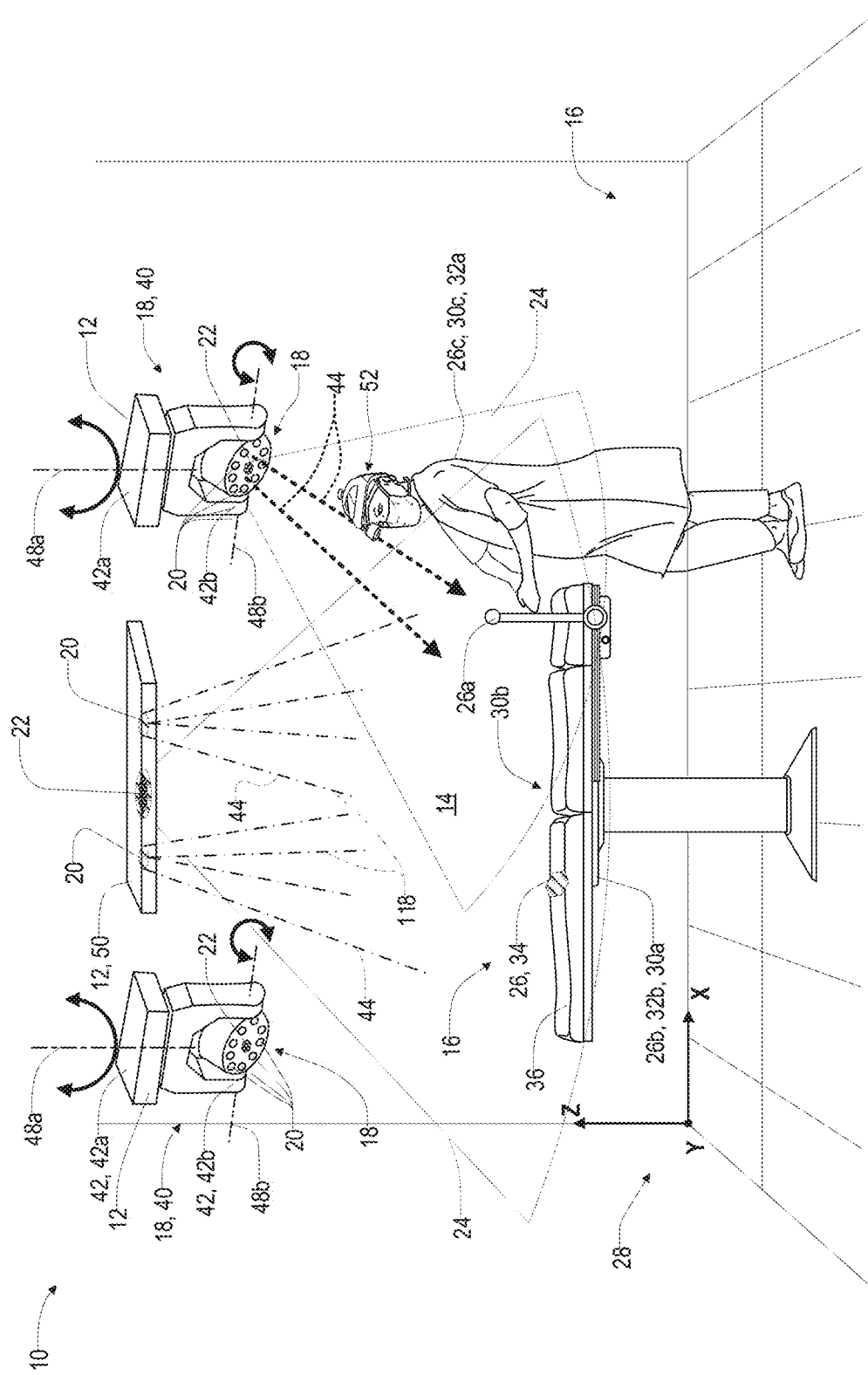
FIG. 1 is a schematic view of a medical suite comprising an illumination system.

For purposes of description herein, the terms "upper," "lower," "right," "left," "rear," "front," "vertical," "horizontal," and derivatives thereof shall relate to the invention as oriented in FIG. 1. Unless stated otherwise, the term "front" shall refer to the surface of the element closer to an intended viewer of the display mirror, and the term "rear" shall refer to the surface of the element further from the intended viewer of the display mirror. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a ..." does not, without more constraints, preclude the existence of additional identical elements in the process, method, article, or apparatus that comprises the element.

Figure 2:
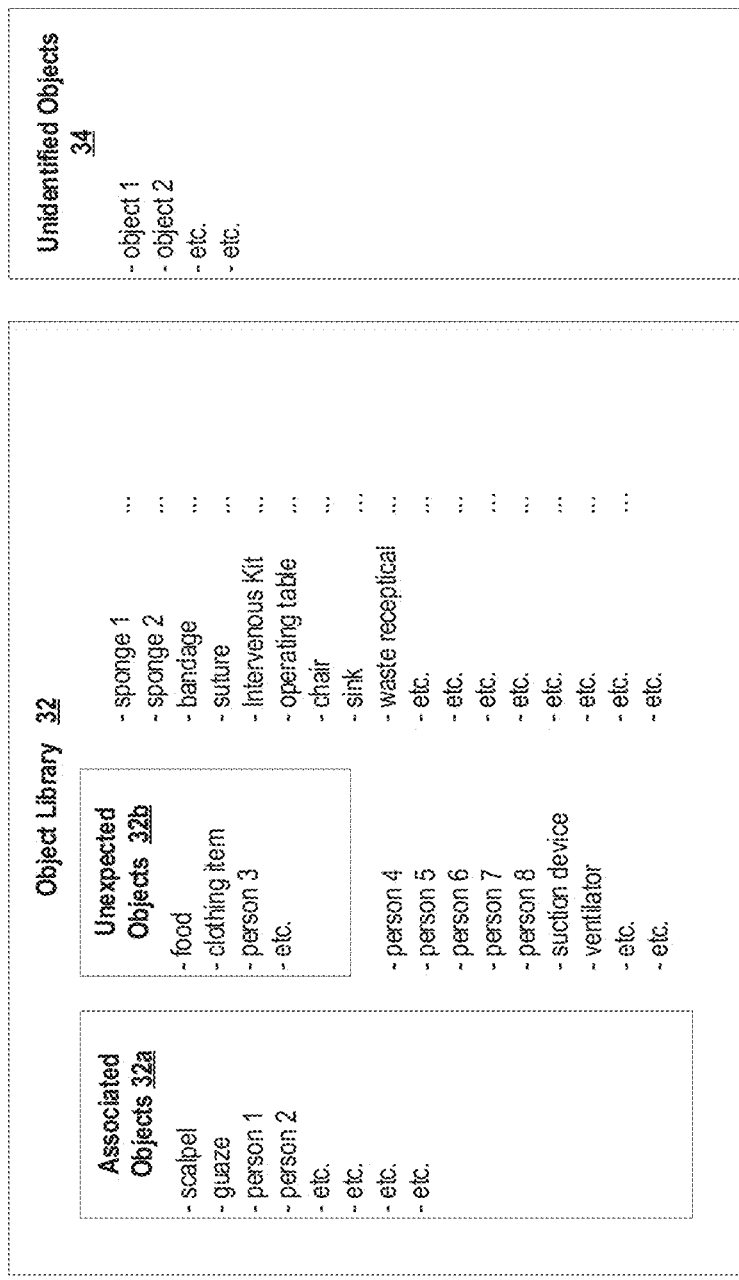
FIG. 2 is a block diagram demonstrating an object library implemented for the identification of objects by the illumination system.

Referring generally to FIGS. 1-2, the disclosure provides for an illumination system 10 configured to track the activity of the operating environment in which it is implemented. In various examples, the illumination system 10 may comprise a controller 12 and various accessories that may be utilized in a medical suite 14 to selectively illuminate a location or operating region 16. Accordingly, illumination system 10 may comprise one or more light assemblies 18, which may include one or more light sources 20. Additionally, the system 10 implements at least one imager 22 or scanning device to capture image data or tracking data in a field of view 24 comprising the operating region 16. In some implementations, the system 10 may comprise a plurality of the imagers 22 configured to track activity throughout the operating region 16. In this way, the system 10 may be configured to detect and track activity over a plurality of fields of view, which may be stitched together or otherwise tracked in combination by one or more of the controllers 12 to monitor activity of persons, items, accessories and any objects that may be captured in the image data of the imagers 22.

In operation, the controller(s) 12 of the system 10 may be configured to scan the operating region 16 to identify each of a plurality of objects 26, which may correspond to medical implements 26a (e.g., tools, accessories, inventory items, etc.), medical equipment or devices 26b, persons 26c (e.g., physicians, nurses, staff, etc.), and any other objects 26 that may be detected in the image data. Once the objects 26 are detected, the system 10 may track the items within the operating region 16 based on the location of the objects 26 detected within the field(s) of view 24 of the one or more imagers 22. In order to track the location of the objects 26 among multiple imagers 22, the system 10 may be configured to identify the location of the objects 26 in grid or coordinate system 28. Accordingly, each of the imagers 22 may be calibrated and programmed to identify a location of each identified object 26 within the coordinate system 28 and register the object 26 for tracking among the multiple fields of view 24, such that the location of the object 26 may be tracked and documented over time. In this way, the system 10 may provide for inventory and personnel tracking, which may be implemented to improve efficiency, reduce waste, and document activity. Additionally, while tracking such activity, the system 10 may control the light assemblies 18 to ensure that one or more of the objects 26 designated for illumination is consistently and effectively illuminated as the objects move through the operating region 16.

In order to identify persons 26c, the system 10 may be configured to capture and process identifying information related to a patient, operation, or task that may be undertaken by a user in the medical suite 14. The identifying information may correspond to biometric information that may be processed by the controller 12 of the system 10 to determine an identity of the patient via one or more identification methods (e.g. facial recognition, iris recognition, fingerprint recognition, etc.) Accordingly, each of the imagers 22 of the system 10 may operate as a scanning apparatus configured to capture the identifying information (e.g. biometric, identification number, coded identifiers, etc.) in the operating region 16. In this way, the system 10 may provide for detection and tracking of one or more persons 26c in the operating region 16.

As previously discussed, once an object 26 is identified by the system 10, a position and the related activity of the object 26 may be tracked and inferred within the coordinate system 28 via the image data. In examples where the system 10 is configured to track multiple objects 26, the tracking information for the objects 26 may be referred to herein as logistic data, which may include an absolute location in relation to the coordinate system 28, relative location (e.g. in relation to a person or object of interest 30 located in the operating region 16), and presence or inventory information. Based on the logistic data, each of the objects 26 may be tracked over time in the fields of view 24, such that changes in the position or motion of the objects 26 may be tracked and analyzed by the system 10.

In relation to inventory or tracking of the objects 26, the system 10 may be configured to track the objects 26 and complete a balance determination or accounting for each of the objects 26 detected in the image data. For example, the controller(s) 12 may be configured to access object data or information from memory, a databased, and/or a remote server to determine assigned storage, implant, and/or disposal information for each of the objects 26 detected. Accordingly, as the system 10 tracks the objects 26, the controller(s) 12 may track the locations of the objects 26 and complete an accounting or balance determination, which may identify the introduction of the objects 26 into the operating region as well as track intermediate and final locations of the objects in a disposal, storage, or implant location. Based on the identified locations of the objects 26, the controller(s) 12 may compare the locations to assigned locations identified in the object data or information. If one or more objects are not placed in an assigned location or an object that was introduced cannot be accounted for, the controller(s) 12 may identify an imbalance or accounting error indicating that the one or more objects are not positioned in the assigned location associated with the object. In this way, the controller(s) 12 may track the objects 26 and provide alerts for objects 26 that are misplaced or unaccounted for.

With the location of the objects 26 detected and tracked in the operating region 16, the system 10 may be operable to provide a number of beneficial operations. For example, the system 10 may be configured to control and adjust the lighting to ensure uniform illumination is provide to a target region 30a, critical object 30b, and/or tracked person 30c, each of which may move within the operating region 16. Additionally, the system 10 may be configured to track the presence, position, and motion of the objects to track or analyze workflow. For example, as further discussed in reference to FIG. 4, system 10 may be configured to track the position of each person 26c in the operating region 16. Once captured, the motion of the persons 26c may be utilized by the system to alert excess motion and identify inefficiencies occurring in the operating region 16 to provide complex workflow tracking for process improvement. Additionally, the system 10 may be configured to identify and address limitations of the light assemblies 18, which may be associated with the inability to illuminate the object of interest 30 or multiple objects 26 simultaneously (e.g. automatically illuminating a plurality of targets or objects). Accordingly, the disclosure provides for systems and methods that may be configured to track and optimize complex workflows, identify motion patterns of the objects 26, track and illuminate the objects 26 moving in the operating region 16 in real time, and various forms of dynamic lighting operations. Accordingly, the disclosure provides for a multifunctional illumination system 10 that may be scaled to suit various applications and implemented to provide a variety of operating features.

Still referring to FIGS. 1 and 2, the system 10 may be configured to process the image data to identify objects based on a computer vision algorithm and an associated object library 32. Accordingly, each of the objects that may be identified by the system 10 may be registered in the object library 32. Additionally, the system 10 may be configured to distinguish objects 26 identified in the object library 32 into various categories. For example, authorized, permitted, or expected items (e.g., those commonly used in the operating region 16) may be identified by the system 10. Such objects 26 may be distinguished from others because they are introduced into the operating region 16 in accordance with a tracked inventory or preapproved for use in the operating region 16 in relation to a specific procedure activity, a room or zone of operation, or environment of the system 10. Such objects 26 may be referred to as associated objects 32a in accordance with predetermined association with the operating region 16. Accordingly, the system 10 may be configured to identify and track a wide variety of the objects 26 and categorize the objects 26. However, not all of the objects 26 that may be identified, may be authorized or identified for use in the operating region 16.

In some implementations, the system 10 may be configured to detect unauthorized or unrelated objects 26 that may not be included in the list of associated objects 32a. Such items may be referred to herein as unexpected objects 32b and may be those that are identifiable via the processing of the image data of the system 10 but not expected based on the tracked inventory or objects 26 associated with the operating region 16. Examples of such unexpected objects 32b or unauthorized items may include food products, unregistered tools, personal items, non-conforming attire or personal accessories (e.g., clothing, jewelry, etc.), unauthorized persons, or any other objects that may be identified by one or more computer vision algorithms operating on one or more controllers 12 of the system 10. Further detailed discussion of the operations of the system 10 and the one or more controllers 12 is provided in reference to FIG. 5.

In some implementations, the system 10 may be configured to project a narrow emission of light, for example a spotlight, into the operating region 16 emphasizing or otherwise illuminating one or more of the objects 26. The proportions of the emission forming the spotlight may be adjusted (e.g. varied in formation or proportion through a lens or aperture) to enlarge or focus the surface or object 26 illuminated by the light sources 20. In some cases, the proportions of the spotlight or beam may be adjusted based on the appearance of the corresponding light represented in the image data. Accordingly, the system 10 may be configured to illuminate the object 26 and adjust the proportions or pattern of the incident light to illuminate the object 26 while truncating the light extending beyond the boundaries of the object 26. In this way, the system 10 may project a spotlight to illuminate the object 26 based on a position identified in the image data and adjust the proportions or illumination pattern of the light sources 20 to extend to a boundary of the object as identified in the image data. Such an automated lighting operation may visually emphasize one or more of the objects 26.

For example, in response to identifying the unexpected object 32b or any detected object 26 as discussed herein, the controller(s) 12 may be configured to direct one or more of the emissions 44 from the light sources 20 to illuminate a location in the one or more fields of view 24 where an object is detected. Additionally, the system 10 may be configured to track changes in the position of the object in the image data and control a positioning assembly of the light assembly 18 to track and illuminate the object 26 as it moves in the operating region 16. In some cases, the object 26 may be the critical object 30b, the tracked person 30c, the unexpected object 32b, an unidentified object or various objects or areas that may be identified in the image data. Additionally, the light sources 20 may be configured to illuminate the objects 26 in the operating region 16 in a first emission having first color and second emission having a second color. In this configuration, the system 10 may be configured to illuminate a first object or target area in a first color and a second object in a second color.

In addition to the associated objects 32a and the unexpected objects 32b, the system 10 may further be configured to detect, track, and/or document unidentified objects 34. Such objects may be those that are detected in the image data but are not associated with objects defined in the object library 32. In response to the detection of the unidentified objects 34, the system 10 may document one or more characteristic features (e.g., lines, text, coded information) or visible features in combination such that the unidentified objects may be documented in a memory or database along with images data recording the detection. Though the identify of such unidentified objects 34 may not be immediately determined by the computer vision algorithms of the system 10, the location of the associated characteristic features may be tracked and documented by the system 10. Additionally, the image data and characteristic features of the unidentified objects 34 that are documented by the system 10 may be utilized as training data to expand the object library 32. In this way, the system 10 may be configured to improve its operational efficacy and performance over time by improving the object library 32. Such additions to the object library 32 may be maintained privately by an owner of the system 10 or may be uploaded to a central database to improve the operation of each installation of the systems 10 discussed herein.

Referring now to FIG. 1, as depicted, the illumination system 10 a plurality of the light assemblies 18. Each of the light assemblies 18 may be implemented via articulating light sources 20 incorporated in a fixed housing and/or light sources connected to gimballed or articulating arms as discussed herein. The illumination system 10 may include one or more of the imagers 22 depicted to direct illumination toward the target region 30a, critical object 30b, and/or tracked person 30c, etc. The imagers 22 may be positioned within or coupled to the light assemblies 18 (e.g., in handles or bodies), a table 36, and/or around the medical suite 14. The imager 22 may be a charge-coupled device (CCD) imager, a complementary metal-oxide-semiconductor (CMOS) imager, other types of imagers, and/or combinations thereof. According to various examples, the imager 22 may include one or more lenses to collimate and/or focus the light reflected by the patient, the table 36, or other features of the medical suite 14.

The table 36 may at least partially define the operating region 16. Although described in connection with the medical suite 14, it will be understood that the illumination system 10 of the present disclosure may be utilized in a variety of environments. For example, the illumination system 10 may be utilized in automobile repair areas, doctor's offices, dentistry, photography studios, manufacturing settings, as well as other areas where dynamic lighting solutions may be advantageous.

The light assemblies 18 may take a variety of configurations. The light assemblies may include one or more light sources 20. In a first example, the light assemblies 18 may be modular and interconnected and supported on a track system. For example, the light assemblies 18 may have a circular, oval, oblong, triangular, square, rectangular, pentagonal or higher order polygon shape. It will be understood that different light assemblies 18 may be provided in different forms and that the illumination system 10 may include a variety of light assemblies 18.

In various implementations, the light sources 20 may be configured to emit light in various wavelengths throughout the operating region 16. For example, the light sources 20 may include a range of emitters (e.g., light emitting diodes, etc.) that may be controlled by the system 10 to emit light in various wavelengths, which may range from infrared to ultraviolet and include the visible spectrum of wavelengths. In some embodiments, the light emitted from the light sources may be emitted as infrared light (e.g., near-infrared, infrared, and/or far-infrared). In other embodiments, visible light may be emitted to illuminate the operating region 16. Accordingly, the lighting assemblies 18 may be flexibly applied to provide for various lighting operations including uniform illumination within the operating region 16. Additionally, the systems discussed herein may provide support to various applications of machine vision including object detection, recognition, tracking, inventory, and various other vision related applications. A detailed example of an illumination method and related systems that may be implemented by the lighting assemblies and systems discussed herein is provided in U.S. Pat. No. 10,240,751 B2, "SYSTEMS AND METHODS OF ILLUMINATION", the disclosure of which is incorporated herein by reference in its entirety.

In some implementations, system 10 may control and adjust the light emitted from the light sources to enhance the image data captured by the imagers 22. For example, the controller 12 of the lighting assembly may adjust the emission of light output from the light source(s) 20 to include various wavelengths of light, which may cause types of objects 26 to stand out or appear with improved intensity or detail in the image data. Accordingly, the illumination system 10 may be configured to adjust the wavelengths of light emitted into the operating region over time in order to cause objects 26 or fluids, biological materials, etc. to be emphasized in relation to their light reflective properties. Accordingly, the system 10 may utilize the variations in illumination to assist in the identification of the objects 26 in the image data. In this way, the illumination system 10 may be flexibly applied to provide for various lighting operations and detection of the objects 26.

In various examples, the light assemblies 18 may be positioned or suspended from one or more positioning assemblies 40, which may adjust a projection direction of the light sources 20 by controlling one or more actuators 42. Accordingly, the positioning assemblies may be configured to rotate and/or translate independently or in any combination. As shown, the system 10 may comprise a first positioning mechanism and a second positioning mechanism. In general, the positioning assemblies 40 as discussed herein may be configured to control a direction of one or more lighting emissions 44 emitted from light sources 20. As demonstrated and further discussed further herein, each of the light sources 20 as well as the positioning assemblies 40 may be in communication with the controller 12, which may be configured to control a direction of the one or more lighting emissions 44 to illuminate target region 30*a*, critical object 30*b*, and/or tracked person 30*c*.

In various embodiments, the one or more positioning assemblies 40 may comprise one or more gimbaled arms, which may be maneuvered or adjusted in response to a movement (e.g., rotational actuation) of one or more actuators 42*a* and 42*b*. In this configuration, the controller 12 may be configured to control each of the actuators 42*a* and 42*b* to manipulate the orientation of the lighting assemblies 18. In this way, the positioning assembly 40 may control the rotation of the lighting assemblies 18 about a first axis 48*a* and a second axis 48*b*. Such manipulation of the actuators 42*a*, 42*b* may enable the controller 12 to direct the light sources 20 to selectively illuminate the operating region 16 or various portions of the medical suite 14.

The positioning assemblies 40 and actuators 42*a* and 42*b*, as discussed herein, may correspond to one or more electrical motors (e.g., servo motors, stepper motors, etc.). Accordingly, each of the positioning assemblies 40 (e.g., the actuators 42) may be configured to rotate the lighting module 360 degrees or within the boundary constraints of lighting assemblies 18 or other support structures that may support the lighting assemblies 18. The controller 12 may control the motors or actuators 42 of the lighting assemblies 18 to direct the lighting emissions 44 of the light sources 20 to target a desired location in the medical suite 14. In order to accurately direct the lighting module 46 to the desired location, the controller 12 may be calibrated to control the position of the lighting module 46 to target locations in the coordinate system 28 of the medical suite 14. The calibration of such a system may require maintenance in the form of calibration updates or compensation due to variations in operation of the positioning assemblies 40 and actuators 42 that may occur over time.

Figure 3:
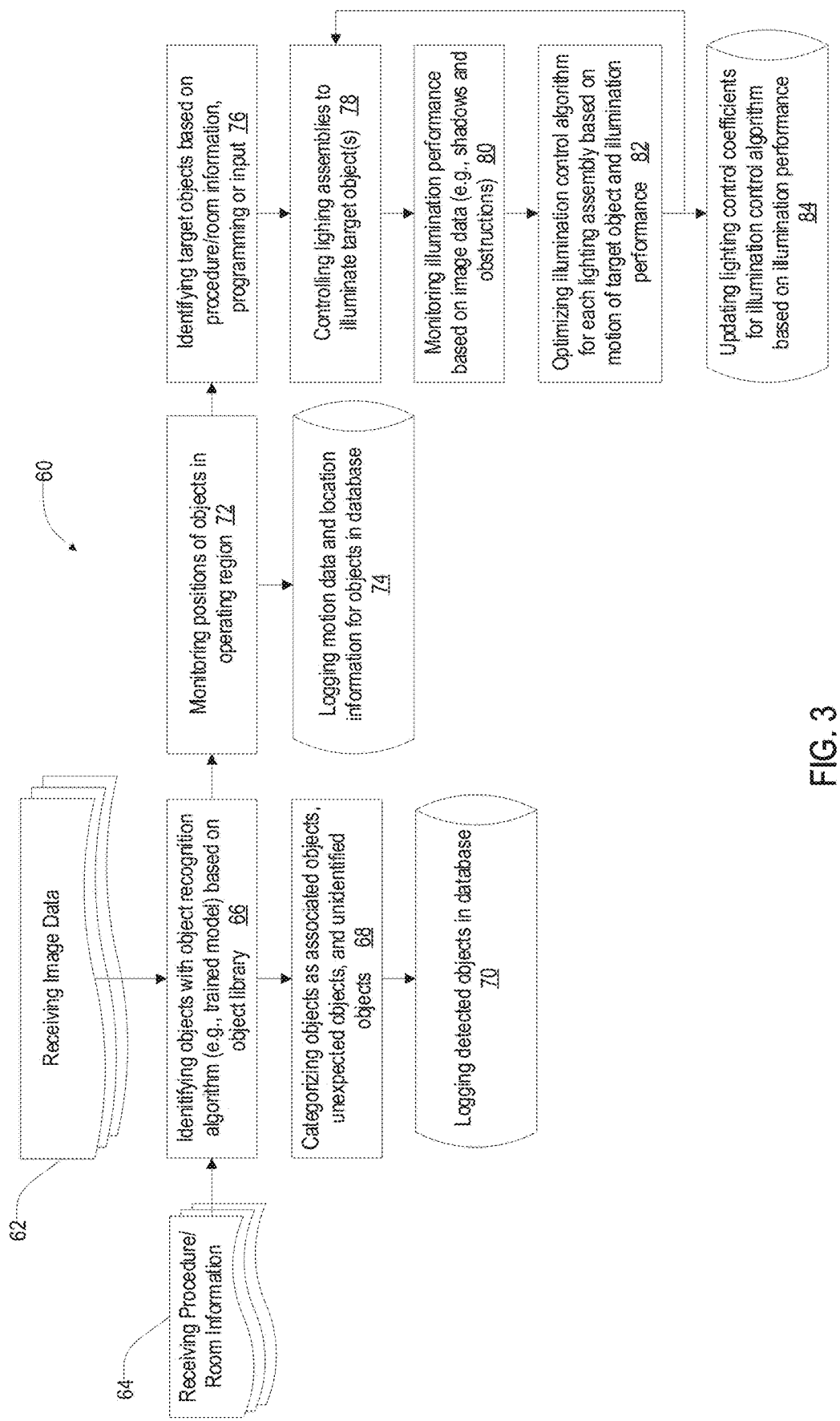
FIG. 3 is a flowchart demonstrating a control method for an illumination system.

Referring now to FIGS. 1 and 3, in some embodiments, the illumination system 10 may process the image data to detect the objects 26 and control the illumination of the lighting assemblies 18. The imagers 22 may be configured to relay image data to the controller 12 of the illumination system 10. The controller 12 may include a memory and a processor. The memory may store computer executable commands (e.g., routines) which are controlled by the processor. According to various examples, the memory may include a light control routine and/or an image analyzing routine. The image analyzing routine is configured to process data from the imagers 22. For example, the image analyzing routine may be configured to identify shadows and luminosity of the operating region 16, the light from the guidance system, location of points of interest (e.g., users around the table 36) and/or gestures from the users. Additionally, the controller 12 may be configured to apply one of more object detection algorithms including, but not limited to, detection models trained via machine learning or various pre-trained detection models, which may be implemented to identify the objects 26 defined in the library 32. Examples of pre-trained models that may be implemented for the identification of the objects may include, but are not limited to, the following: LeNet, AlexNet, ZF Net, GoogleNet, VGG-Net, ResNet, etc. Once the image analyzing routine has processed the data from the imager(s) 22, the light control routine may control how the positioning assemblies 40 are operated. For example, the light control routine may be configured to move, steer, activate or otherwise influence the light assemblies 18 to emit light at the location of the target region 30*a*, critical object 30*b*, and/or tracked person 30*c*.

Though the imagers 22 are discussed as being incorporated on each of the lighting assemblies 18, the system 10 may be configured to capture image data from any location in the medical suite 14. In order to process and coordinate the image data from each of the imagers 22 and the operation of the lighting assemblies 18, each of the controllers 12 may be in communication with and controlled via a central controller 50. In such embodiments, the central controller 50 may be configured to process the image data from the one or more imagers 22 and communicate control signals for each of the plurality of lighting assemblies and the actuators 42 of the positioning assemblies 40. Accordingly, the system 10 may be implemented in a variety of beneficial embodiments without departing from the spirit of the disclosure.

Though discussed in specific reference to the controllers 12 and the central controller 50, many of the various operations of the systems and apparatuses discussed herein may operate based on one or more computerized control devices that may generally be referred to herein as the controller 12. It shall be understood that the term "controller" as described may refer to variety of processing modules (e.g. processors, microprocessors, integrated circuits, etc.), which may be in communication with one or more memory devices, databases, servers, etc. in order to control the various operations described herein. Further description regarding the controller 12 and the operations of the systems discussed herein are provided in further detail in reference to FIG. 5.

In some embodiments, the system 10 may additional process the image data to identify one or more obstructions 52 that may interfere with the light emitted from the light sources 20 from impinging upon the target region 30a, critical object 30b, and/or tracked person 30c. The obstructions 52 may be identified in response to detecting one or more pulsed infrared emissions emitted from the lighting assemblies 18. For example, the central controller 50 may be calibrated to identify an approximate location of the point the location on which the infrared emissions intersect the obstructions 52 by processing the image data in reference to the coordinate system 28. In this way, the central controller 50 may detect a location of the obstructions 52 in relation to the coordinate system 28, such that an alternate trajectory of the light may be calculated and monitored in the image data to successfully illuminate the target region 30a, critical object 30b, and/or tracked person 30c.

Referring to FIG. 3, a flowchart for a method 60 for controlling the system 10 is demonstrated. In operation, the method 60 may begin in response to the controller 12 receiving image data 62 from the imagers 22. Additionally, the controller 12 may also receiving programming information 64 that may identify the associated objects 32a of the object library 32 associated with a specific procedure activity, a room or zone of operation, or environment of the system 10. Once received, the controller may begin processing the image data 62 and identifying the objects 26 detected in the operating region 16 based on one or more object recognition algorithms as discussed herein (66). As previously discussed, the objects 26 detected in the operating region 16 may be categorized as associated objects 32a, unexpected objects 32b, and unidentified objects 34 (68). Additionally, the objects 26 may be classified as being associated with a target region 30a, critical objects 30b, and/or tracked persons 30c, each of which may be prioritized to illumination via a lighting algorithm and/or tracked and analyzed for various purposes. Accordingly, the objects 26 detected in the operating region 16 may be categorized and tracked over time and logged into memory or a database to provide information regarding activities completed in the operating region 16 (70).

As previously discussed, the unidentified objects 34 may be tracked based on one or more characteristic features (e.g., lines, text, coded information) or visible features in combination. In this way, the unidentified objects 34 may be documented in a memory or database along with images data recording the detection in step 70. Additionally, the object recognition or computer vision algorithms of the system 10 may utilize the image data 62 and motion data captured for the unidentified objects 34 as training data to expand the object library 32. In this way, the system 10 may be configured to improve its operational efficacy and performance over time by improving the object library 32. Such additions to the object library 32 may be maintained privately by an owner of the system 10 or may be uploaded to a central database to improve the operation of each installation of the systems 10 discussed herein.

Once the objects 26 are detected in the image data 62, the system 10 may continue to monitor the positions and motion of the objects 26 (72). Once identified, the controller may further record and log the position and motion data for each of the objects 26 in a memory or database (74). The motion and location tracking may be utilized for inventory and personnel tracking, which may be implemented to improve efficiency, reduce waste, and document activity. Additionally, while tracking such activity, the system 10 may control the light assemblies 18 to ensure that one or more of the objects 26 designated for illumination is consistently and effectively illuminated as discussed in reference to steps 76-80.

With the objects 26 identified, the system 10 may further track the location of the objects 26 and prioritize the illumination of the target region 30a, critical objects 30b, and/or tracked persons 30c (76). With the location and priority of the objects 26 determined, the controller(s) 12 of the system 10 may control the actuators 42 of the positioning assemblies 40 to direct the lighting assemblies 18 to illuminate the objects 26 (78). While illuminating the objects 26, the controller(s) 12 may continue to monitor the image data to determine and improve the illumination performance of the lighting assemblies by reducing inconsistencies, mitigating shadows, and identifying unobstructed paths from the lighting assemblies 18 to the objects 26 to limit interference by obstructions (80). Based on the detected inconsistencies, shadows, and obstructions, the method 60 may continue to optimize the illumination of the operating region 16 by optimizing illumination control algorithm for each lighting assembly based on the image data, which may also be utilized to track the motion of target region 30a, critical objects 30b, and/or tracked persons 30c (82). Additionally, the method 60 may update lighting control coefficients of the lighting algorithm or associated trained models for recognition of the objects to optimize the illumination and detection performance of the system 10 (84).

Figure 4:
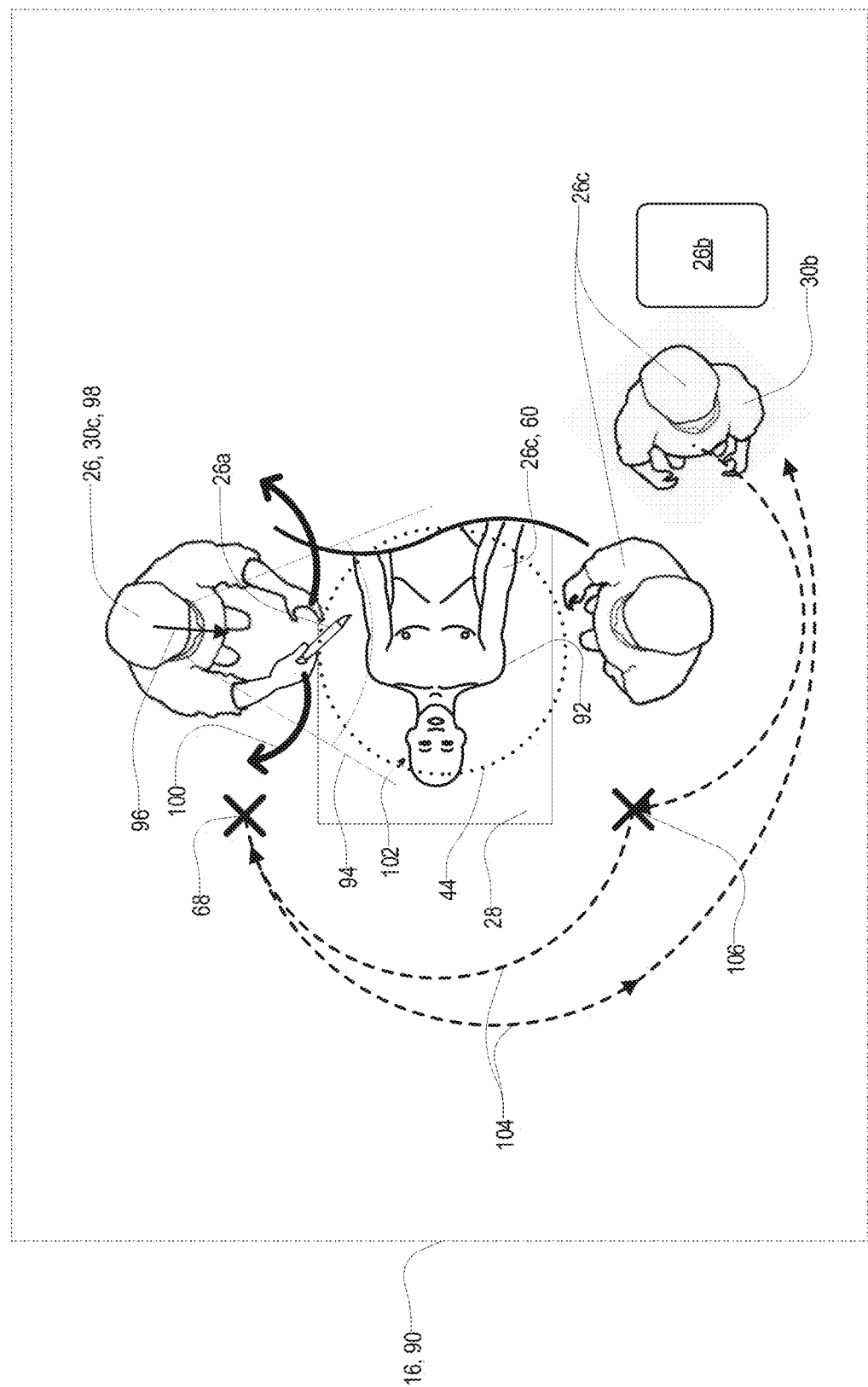
FIG. 4 is an illustrative diagram demonstrating activities and tracking techniques applied by an illumination system to prioritize the illumination of an operating region.

Referring to FIG. 4, an elevational view of an exemplary operating region 90 for the illumination system 10 is shown demonstrating a lighting routine and object tracking operation. As illustrated, FIG. 4 demonstrates a plurality of persons 26c positioned within the operating region 16. As previously discussed, the illumination system 10 may be configured to provide consistent illumination of a target region 30a, which in this case includes a critical object 30b in the form of a patient 92. In this configuration, the controller(s) of the lighting assemblies 18 may prioritize the illumination of the target region 30a and may further prioritize the illumination of the patient 92 or a designated portion or critical object 30b within the target region 30a. Prioritization as discussed herein indicates the relative importance or order of importance of the target regions 30a and/or objects 26 to illuminate. Based on the prioritization among the objects 26 and/or target regions 30a, the controller(s) 12 of the system 10 can selectively control the lighting assemblies 18 and best apply the lighting resources (e.g., the number of and range of the emissions 44) to select which target regions 30a and/or objects 26 to illuminate the identified aspects of the operating region 16 in the prioritized order. In this way, the system 10 may monitor the targeted regions and objects 26 of the operating region 16 for illumination and prioritize the illumination based on the available lighting resources (e.g. the quantity, location, and range of illumination of the lighting assemblies 18).

In some implementations, the target region 30a for illumination may include a line of sight or focus region 94, which may be defined as a gaze direction 96 of a person 26c in the operating region 16. For example, the gaze direction 96 of a surgeon 98 or other tracked persons 30c may be determined based on the location of the person 26c and an orientation 100 of a head of the person 26c. The orientation 100 or angle of the head may be identified by one or more features in the image data (e.g., eyes, brow, nose, etc.) as an angular direction or gaze direction 96 relative to the location of the person 26c. Accordingly, the illumination system 10 may track the gaze direction 96 and target the illumination resources to illuminate a region within a predetermined proximity of the person 26c or surgeon 98 along the gaze direction 96. Similarly, the illumination system 10 may track the gaze direction 96 and illuminate a portion of the operating region 16 which includes an intersection 102 between the gaze direction 96 and the target region 30a or objects 26. In this way, the controller(s) 12 of the system 10 may prioritize the gaze direction 96 of a person 26c within the target region 30a to further prioritize the illumination of the operating region 16.

As previously discussed, in some cases, the system 10 may also be configured to track the motion of the persons 26c, for example a tracked person 30c, within operating region 16. As shown in FIG. 4, the controller(s) 12 of the system 10 may be configured to track and record a path 104, inflection or standing locations 106, and the distance traveled by the tracked person 30c. In this way, the system 10 may be configured to record the movement statistics of the tracked person 30c based on the changes in location of the person 26c identified in the image data. In some cases, the illumination system 10 may utilize the identified location to illuminate the path 104 as part of a lighting scheme for the operating region 16. However, the system 10 may further utilize the motion statistics to identify the objects 26 in the operating region 16 that move the most in order to flag excessive or repetitive movement of persons 26c. In some cases to the system 10 may identify the coordinated movements of the tracked person 30c in relation objects 26 or persons 26c (e.g., the surgeon 98, leader, etc.) to suggest optimized positions for the objects 26 or persons 26c to limit unnecessary movement. Accordingly, the system 10 may provide for numerous tracking and analyzing operations to identify areas for improvement or automatically suggest relocation positions for the objects 26 to limit the motion in the operating region 16.

Figure 5:
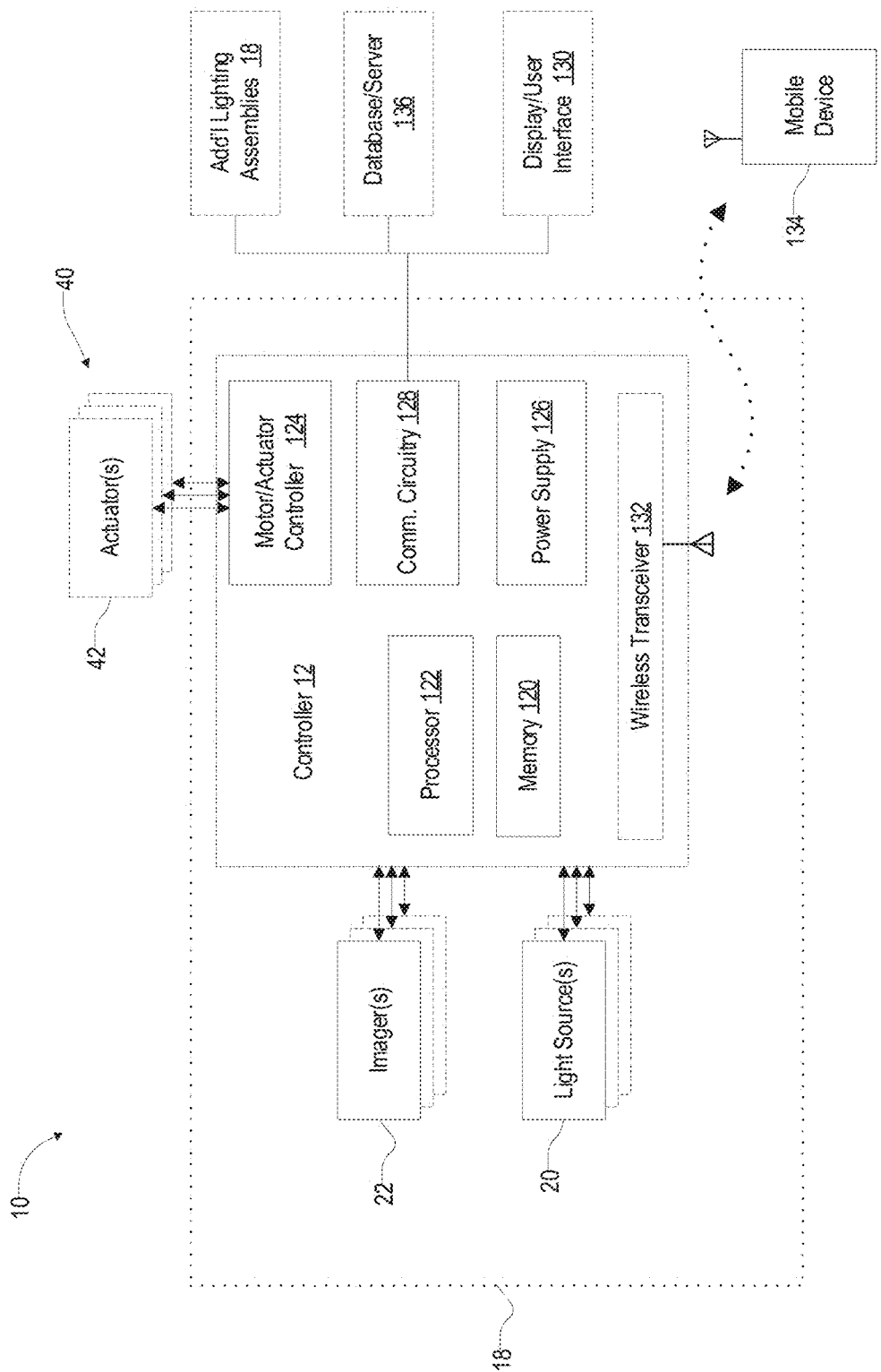
FIG. 5 is a block diagram demonstrating an illumination system in accordance with the disclosure.

Referring to FIG. 5, a block diagram of an illumination system 10 is shown. As discussed herein, the illumination system 10 may include one or more imagers 22 configured to capture image data from the medical suite 14 and/or from the operating region 16. The imagers 22 may be configured to relay visual information to the controller 12 of the illumination system 10. The controller 12 may include a memory 120 and a processor 122. The memory 120 may store computer executable commands (e.g., routines), which are controlled by the processor 122. According to various examples, the memory 120 may include a light control routine and/or an image analyzing routine. In exemplary embodiments, the memory 120 may include the control method 60.

Once the image analyzing routine has processed the image data from the imager 22, the controller 12 may communicate one or more control instructions to a motor or actuator controller 124. In response to the control signals, the actuator controller 124 may control the actuators 42 or the positioning assemblies 40 to move, steer, or otherwise adjust an orientation of the light assemblies 18. In this way, the controller 12 may direct the lighting assemblies 18 to emit the lighting emission 44 and/or direct the field of view 24 to a desired location, which may correspond to the location of the various objects or target areas as discussed herein. The system 10 may additionally comprise one or more power supplies 126. The power supplies 126 may provide for one or more power supplies or ballasts for various components of the lighting assemblies 18 as well as the actuators 42 or positioning assemblies 40.

As discussed herein the controller 12 and/or the central controller 50 may comprise one or more processors 122. The processor(s) 122 may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions, such as one or more application, utilities, an operating system and/or other instructions. The memory 120 may be a single memory device or a plurality of memory devices that are either on-chip or off-chip. Such a memory device may be a read-only memory, random access memory, volatile memory, non-volatile memory, static memory, dynamic memory, flash memory, and/or any device that stores digital information. Accordingly, each of the processing and control steps discussed herein may be completed by one or more of the processors or processing units as discussed herein based on one or more routines, algorithms, processes, etc. that may be accessed in the memory 120.

In some embodiments, the system 10 may further comprise one or more communication circuits 128, which may be in communication with the processor 122. The communication circuit 128 may be configured to communicate data and control information to a display or user interface 130 for operating the system 10. The interface 130 may comprise one or more input or operational elements configured to control the system 10 and communicate data. The communication circuit 128 may further be in communication with additional lighting assemblies 18, which may operate in combination as an array of lighting assemblies. The communication circuit 128 may be configured to communicate via various communication protocols. For example, communication protocols may correspond to process automation protocols, industrial system protocols, vehicle protocol buses, consumer communication protocols, etc. Additional protocols may include, MODBUS, PROFIBUS, CAN bus, DATA HIGHWAY, DeviceNet, Digital multiplexing (DMX512), or various forms of communication standards.

In various embodiments, the system 10 may comprise a variety of additional circuits, peripheral devices, and/or accessories, which may be incorporated into the system 10 to provide various functions. For example, in some embodiments, the system 10 may comprise a wireless transceiver 132 configured to communicate with a mobile device 134. In such embodiments, the wireless transceiver 132 may operate similar to the communication circuit 128 and communicate data and control information for operating the system 10 to a display or user interface of the mobile device 134. The wireless transceiver 132 may communicate with the mobile device 134 via one or more wireless protocols (e.g. Bluetooth®; Wi-Fi (802.11a, b, g, n, etc.); ZigBee®; and Z-Wave®; etc.). In such embodiments, the mobile device 134 may correspond to a smartphone, tablet, personal data assistant (PDA), laptop, etc.

As discussed herein, the system 10 may comprise or be in communication with one or more servers or remote databases 136. The remote database 136 may correspond to a patient database, which may comprise identifying information configured to authenticate the identity of the patient 92. The controller 12 of the system 10 may be in communication with the remote database 136 via the communication circuit 128 and/or the wireless transceiver 132. In this configuration, once the scanning or image data is captured, the controller 12 may be configured to identify one or more of the objects via identification templates or processing resources available the remote database 136.

In various embodiments, the light sources 20 may be configured to produce un-polarized and/or polarized light of one handedness including, but not limited to, certain liquid crystal displays (LCDs), laser diodes, light-emitting diodes (LEDs), incandescent light sources, gas discharge lamps (e.g., xenon, neon, mercury), halogen light sources, and/or organic light-emitting diodes (OLEDs). In polarized light examples of the light sources 20, the light sources 20 are configured to emit a first handedness polarization of light. According to various examples, the first handedness polarization of light may have a circular polarization and/or an elliptical polarization. In electrodynamics, circular polarization of light is a polarization state in which, at each point, the electric field of the light wave has a constant magnitude, but its direction rotates with time at a steady rate in a plane perpendicular to the direction of the wave.

As discussed, the light assemblies 18 may include one or more of the light sources 20. In examples including a plurality of light sources 20, the light sources 20 may be arranged in an array. For example, an array of the light sources 20 may include an array of from about 1×2 to about 100×100 and all variations therebetween. As such, the light assemblies 18 including an array of the light sources 20 may be known as pixelated light assemblies 18. The light sources 20 of any of the light assemblies 18 may be fixed or individually articulated. The light sources 20 may all be articulated, a portion may be articulated, or none may be articulated. The light sources 20 may be articulated electromechanically (e.g., by a motor) and/or manually (e.g., by a user). In static, or fixed, examples of the light sources 20, the light sources 20 may be assigned to focus on various predefined points (e.g., on a patient 92 and/or on the table 36).

Modifications of the disclosure will occur to those skilled in the art and to those who make or use the disclosure. Therefore, it is understood that the embodiments shown in the drawings and described above are merely for illustrative purposes and not intended to limit the scope of the disclosure, which is defined by the following claims as interpreted according to the principles of patent law, including the Doctrine of Equivalents.

It will be understood by one having ordinary skill in the art that construction of the described disclosure, and other components, is not limited to any specific material. Other exemplary embodiments of the disclosure disclosed herein may be formed from a wide variety of materials unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system 10 may be varied, and the nature or numeral of adjustment positions provided between the elements may be varied. It should be noted that the elements and/or assemblies of the system 10 may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise. Further, the claims, as set forth below, are incorporated into and constitute part of this Detailed Description.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

What is claimed is:

1. An illumination system for monitoring and illuminating an operating region, the system comprising:
at least one light assembly comprising at least one illumination source configured to selectively direct a light emission in a portion of the operating region;
at least one imager configured to capture image data in a field of view in the operating region;
a controller in communication with the light assembly and the imager, wherein the controller is configured to:
process image data captured in the field of view;
identify a plurality of objects as a plurality of medical implements detected in the image data based on an object library;
track a location of each of the plurality of objects moving about the operating region;
access object information identifying the medical implements for use in the operating region;
track a path of one or more of the objects moving about the operating region;
record the path of the one or more of the objects moving about the operating region over time; and
record movement statistics of the one or more objects identifying the distance traveled.

2. The system according to claim 1, wherein the controller is further configured to:
determine an identity of a plurality of persons in the operating region; and
determine whether the plurality of persons are authorized personnel based on the identity of each of the plurality of persons.

3. The system according to claim 1, wherein the controller is further configured to:
identify a line of sight of at least one person in the image data and control the at least one lighting assembly to illuminate a portion of the line of sight at a predetermined distance from the at least one person.

4. The system according to claim 3, wherein the line of sight is identified in the image data based on a location of the person in the operating region and an orientation of a head of the person.

5. The system according to claim 1, wherein the controller is further configured to:
identify an intersection between a line of sight of at least one person and at least one additional object of the plurality of objects or an area identified in the image data.

6. The system according to claim 5, wherein the controller is further configured to:
control the lighting assembly to illuminate the intersection between the line of sight and the at least one additional object.

7. The system according to claim 1, wherein the controller is further configured to:
detect unidentified objects in the image data that are not included in the object library.

8. The system according to claim 7, wherein the controller is further configured to:
in response to detecting the unidentified objects, record teaching image data including representative characteristics of the unidentified objects, wherein the controller is configured to process the teaching image data and attribute identities to the unidentified objects.

9. The system according to claim 1, wherein the controller is further configured to:
track a distance traveled by the one or more of the objects in the operating region, wherein distance is tracked based on an accumulated motion of the one or more objects moving about the operating region.

10. The system according to claim 9, wherein the controller is further configured to:
categorize objects of the plurality of objects in the operating region based on a total cumulative motion; and
document the categorized objects.

11. The system according to claim 9, wherein the controller is further configured to:
identify one or more repetitive motion objects of the plurality of objects in the operating region based on a repetitive movement of the tracked location of the plurality of objects.

12. An illumination system for monitoring and illuminating an operating region, comprising:
at least one light assembly comprising an illumination source configured to selectively direct a light emission in a portion of the operating region;
at least one imager configured to capture image data in a field of view in the operating region;
a controller in communication with the light assembly and the imager, wherein the controller is configured to:
process image data captured in the field of view;
identify a plurality of objects detected in the image data based on an object library and access object information for the plurality of objects; and
complete a balance determination of each of the plurality of objects over a period of time, wherein the balance determination maintains an accounting of the plurality of objects and assigns an accounting classification for each of the objects, wherein the accounting classification identifies a status of the plurality of objects upon introduction into the operating region or as a final location and the accounting classifications comprise a disposal, a storage, and an implanted location.

13. The system according to claim 12, wherein the balance determination compares the objects identified in the image data to assigned locations identified in the object information, and the controller is further configured to:
identify an imbalance based on the balance determination, wherein the imbalance comprises an indication that one of the objects is unaccounted for based on a determination that the one of the objects is not positioned in the assigned location associated with the object.

14. An Illumination apparatus configured to illuminate an operating region, the apparatus comprising:

at least one light assembly comprising at least one illumination source configured to selectively direct at least one light emission in a portion of the operating region;

at least one imager configured to capture image data in a field of view in the operating region;

a controller in communication with the light assembly and the imager, wherein the controller is configured to:

process image data captured in the field of view;

identify a plurality of objects detected in the image data based on an object library and access object information for the plurality of objects, wherein the object data identifies the plurality of objects as associated objects preapproved for use in the operating region;

compare the identified objects to the associated objects identified in the object information;

based on the comparison, identify an unexpected object in the library that is not identified as preapproved based on the object data; and in response to the identification of the unexpected object, illuminate the unexpected object with the at least one light emission, wherein the at least one illumination source comprises a plurality of illumination sources configured to illuminate objects in the operating region in a first emission having first color and second emission having a second color, wherein the first emission is projected into the operating region and illuminates a target area and the second emission is directed to and illuminates the unexpected object.

15. The system according to claim 14, wherein the controller is further configured to:

detect the unexpected objects as unidentified objects in the image data that are not included in the object library.

16. The system according to claim 14, wherein the plurality of objects identified as associated objects preapproved for use in the operating region are a plurality of medical implements.

* * * * *